(12) United States Patent
Garcia Molina et al.

(10) Patent No.: US 12,023,451 B2
(45) Date of Patent: Jul. 2, 2024

(54) SYSTEMS AND METHODS FOR DELIVERING SENSORY STIMULATION TO FACILITATE SLEEP ONSET

(71) Applicant: KONINKLIJKE PHILIPS N.V., Eindhoven (NL)

(72) Inventors: Gary Nelson Garcia Molina, Madison, WI (US); Boomika Kalyan, Pittsburgh, PA (US); Antonio Aquino, Harrison City, PA (US); Charles Thomas, Monroeville, PA (US); Matthew D. Hogan, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 653 days.

(21) Appl. No.: 17/112,286

(22) Filed: Dec. 4, 2020

(65) Prior Publication Data
US 2021/0205574 A1 Jul. 8, 2021

Related U.S. Application Data

(60) Provisional application No. 62/945,462, filed on Dec. 9, 2019.

(51) Int. Cl.
*A61M 21/02* (2006.01)
*A61B 5/024* (2006.01)
(Continued)

(52) U.S. Cl.
CPC ..... *A61M 21/02* (2013.01); *A61M 2021/0022* (2013.01); *A61M 2205/3303* (2013.01);
(Continued)

(58) Field of Classification Search
CPC .......... A61M 21/02; A61M 2021/0022; A61M 2205/3303; A61M 2205/50;
(Continued)

(56) References Cited

U.S. PATENT DOCUMENTS

| 2002/0035995 A1 | 3/2002 | Schmidt |
| 2015/0224017 A1 | 8/2015 | Graindorge et al. |
| 2020/0219615 A1* | 7/2020 | Rabin ............ A61M 21/00 |

FOREIGN PATENT DOCUMENTS

| CN | 110418598 A | 11/2019 |
| EP | 3181041 A1 | 6/2017 |

(Continued)

OTHER PUBLICATIONS

Amano, T. & Toichi, M., 2016. The role of alternating bilateral stimulation in establishing positive cognition in EMDR therapy: A multi-channel near-infrared spectroscopy study. PLoS One, 11(10), pp. 1-11.

(Continued)

*Primary Examiner* — Thaddeus B Cox
*Assistant Examiner* — Joshua Daryl D Lannu

(57) ABSTRACT

The present disclosure pertains to systems and methods for delivering sensory stimulation to a subject for facilitating sleep onset. The system comprises one or more sensors for generating output signals indicating one or more physiological parameters of a subject; a sensory stimulator for delivering sensory stimulation to the subject; and one or more physical processors configured to: determine an initial state of the subject based on the output signals from the sensor, the initial state corresponding to at least one physiological parameter of the subject; determine one or more stimulation parameters of sensory stimulation to be delivered to the subject by the sensory stimulator based on the initial state of the subject; and cause the sensory stimulator to deliver the sensory stimulation to the subject based on the determined one or more stimulation parameters.

18 Claims, 10 Drawing Sheets

(51) Int. Cl.
 A61B 5/0245 (2006.01)
 A61B 5/0533 (2021.01)
 A61B 5/372 (2021.01)
 A61M 21/00 (2006.01)
(52) U.S. Cl.
 CPC ..... *A61M 2205/50* (2013.01); *A61M 2230/06* (2013.01); *A61M 2230/10* (2013.01)
(58) Field of Classification Search
 CPC .......... A61M 2230/06; A61M 2230/10; A61M 2021/0011; A61M 2021/0027; A61M 2021/0044; A61M 2205/3584; A61M 2205/3592; A61M 2205/502; A61M 2230/14; A61M 2230/63; A61M 2230/04; A61M 2230/18; A61M 2230/40; A61M 2230/50; A61M 2230/60; A61B 5/0533; A61B 5/372; A61B 5/02405; A61B 5/02416; A61B 5/0245; A61B 5/4812; A61B 5/4836; A61N 2/006; A61N 2005/0645
 See application file for complete search history.

(56) References Cited

FOREIGN PATENT DOCUMENTS

| WO | 2005055802 | A2 | | 6/2005 | |
|---|---|---|---|---|---|
| WO | 2014118654 | A1 | | 8/2014 | |
| WO | 2015087188 | A1 | | 6/2015 | |
| WO | 2016087983 | A1 | | 6/2016 | |
| WO | 2016166202 | A1 | | 10/2016 | |
| WO | WO-2016166202 | A1 | * | 10/2016 | ........... A61B 5/0476 |
| WO | 2017173436 | A1 | | 10/2017 | |
| WO | 2019115412 | A1 | | 6/2019 | |
| WO | WO-2019115412 | A1 | * | 6/2019 | ........... A61B 5/1103 |

OTHER PUBLICATIONS

Barralon, P. et al., 2008. Autonomic nervous system response to vibrating and electrical stimuli on the forearm and wrist. In 2008 30th Annual International Conference of the IEEE Engineering in Medicine and Biology Society. pp. 931-934. Available at: http://ieeexplore.ieee.org/document/4649307/.
Burgess, H.J., Kleiman, J. & Trinder, J., 1999. Cardiac activity during sleep onset. Psychophysiology, 36(3), pp. 298-306.
Burgess, H.J., Trinder, J. & Kim, Y., 1996. Cardiac parasympathetic nervous system activity does not increase in anticipation of sleep. Journal of Sleep Research, 5(2), pp. 83-89.
Cellini, N. et al., 2016. Heart rate variability during daytime naps in healthy adults: Autonomic profile and short-term reliability. Psychophysiology, 53(4), pp. 473-481.
Chouchou, F. & Desseilles, M., 2014. Heart rate variability: a tool to explore the sleeping brain? Autonomic Neuroscience, 8(Dec.), pp. 1-9.
Hiraba, H. et al., 2014. Facial vibrotactile stimulation activates the parasympathetic nervous system: Study of salivary secretion, heart rate, pupillary reflex, and functional near-infrared spectroscopy activity. BioMed Research International, 2014.
Miller, C.B. et al., 2016. Clusters of Insomnia Disorder: An Exploratory Cluster Analysis of Objective Sleep Parameters Reveals Differences in Neurocognitive Functioning, Quantitative EEG, and Heart Rate Variability. Sleep, 39(11), pp. 1993-2004. Available at: https://academic.oup.com/sleep/article-lookup/doi/10.5665/sleep.6230.
Murtagh, D.R.R. & Greenwood, K.M., 1995. Identifying Effective Psychological Treatments for Insomnia: A Meta-Analysis. Journal of Consulting and Clinical Psychology, 63(1), pp. 79-89. Available at: https://www.med.upenn.edu/cbti/assets/user-content/documents/MurtaghCBTImeta-analysis.pdf.
Nieuwenhuis, S. et al., 2013. Bilateral saccadic eye movements and tactile stimulation, but not auditory stimulation, enhance memory retrieval. Brain and Cognition, 81(1), pp. 52-56. Available at: http://dx.doi.org/10.1016/j.bandc.2012.10.003.
Okamoto-Mizuno, K. et al., 2008. Heart rate variability and body temperature during the sleep onset period. Sleep and Biological Rhythms, 6(1), pp. 42-49.
Yamaguchi, S. et al., 2014. Assessment of Biological Reaction to Whole Body Vibration Training by Evaluating Changes in Salivary Components and Cutaneous Blood Flow. Health, 6(Apr.), pp. 1049-1056. Available at: http://www.scirp.org/journal/PaperInformation.aspx?PaperID=44927#.U0-bs-Z_uRU.
Serin, A., Hageman, N.S. & Kade, E., 2018. The Therapeutic Effect of Bilateral Alternating Stimulation Tactile Form Technology on the Stress Response. Journal of Biotechnology and Biomedical Science, 1(2), pp. 46-52.
Shaffer, F. & Ginsberg, J.P., 2017. An Overview of Heart Rate Variability Metrics and Norms. Frontiers in Public Health, 5(Sep.), pp. 1-17. Available at: http://journal.frontiersin.org/article/10.3389/fpubh.2017.00258/full.
International Search Report and Written Opinion, International Application No. PCT/EP2020/084347, dated Mar. 11, 2021.

* cited by examiner

SYSTEMS AND METHODS FOR DELIVERING SENSORY STIMULATION TO FACILITATE SLEEP ONSET

CROSS-REFERENCE TO PRIOR APPLICATIONS

This application claims the benefit of European Patent Application No. 62/945,462, filed on 9 Dec. 2019. This application is hereby incorporated by reference herein.

BACKGROUND

1. Field

The present disclosure pertains to a system and method for delivering sensory stimulation to a subject to facilitate sleep onset.

2. Description of the Related Art

Users that need help to fall asleep and use existing tactical sensory TS devices, do not receive recommendation about when and how long they need to use the device to reach an optimal state to fall asleep. They do not know how close from the optimal state they are after having used TS for a given period of time. The present disclosure overcomes deficiencies in prior art systems.

SUMMARY

Accordingly, one or more aspects of the present disclosure relate to a system for delivering sensory stimulation to a subject for facilitating sleep onset. The system comprises one or more sensors configured to generate output signals indicating one or more physiological parameters of a subject; a sensory stimulator configured to deliver sensory stimulation to the subject; and one or more physical processors operatively connected with the one or more sensors and the sensory stimulator, the one or more physical processors being programmed with computer program instructions which, when executed cause the computer system to: determine an initial state of the subject based on the output signals from the sensor, the initial state corresponding to at least one physiological or behavioral parameter of the subject; determine one or more stimulation parameters of sensory stimulation to be delivered to the subject by the sensory stimulator based on the initial state of the subject; and cause the sensory stimulator to deliver the sensory stimulation to the subject based on the determined one or more stimulation parameters.

Another aspect of the present disclosure relates to a method for delivering sensory stimulation to a subject for facilitating sleep onset, comprising: generating, with one or more sensors, output signals indicating one or more physiological parameters of a subject; delivering, with a sensory stimulator, sensory stimulation to the subject; determining, with one or more physical processors, an initial state of the subject based on the output signals from the sensor, the initial state corresponding to at least one physiological parameter of the subject; determining, with one or more physical processors, one or more stimulation parameters of sensory stimulation to be delivered to the subject by the sensory stimulator based on the initial state of the subject; and causing, with one or more physical processors, the sensory stimulator to deliver the sensory stimulation to the subject based on the determined one or more stimulation parameters.

Still another aspect of the present disclosure relates to a system for delivering sensory stimulation to a subject for facilitating sleep onset, comprising: means for generating output signals indicating one or more physiological parameters of a subject; means for delivering sensory stimulation to the subject; means for determining an initial state of the subject based on the output signals from the sensor, the initial state corresponding to at least one physiological parameter of the subject; means for determining one or more stimulation parameters of sensory stimulation to be delivered to the subject by the sensory stimulator based on the initial state of the subject; and means for causing the sensory stimulator to deliver the sensory stimulation to the subject based on the determined one or more stimulation parameters.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
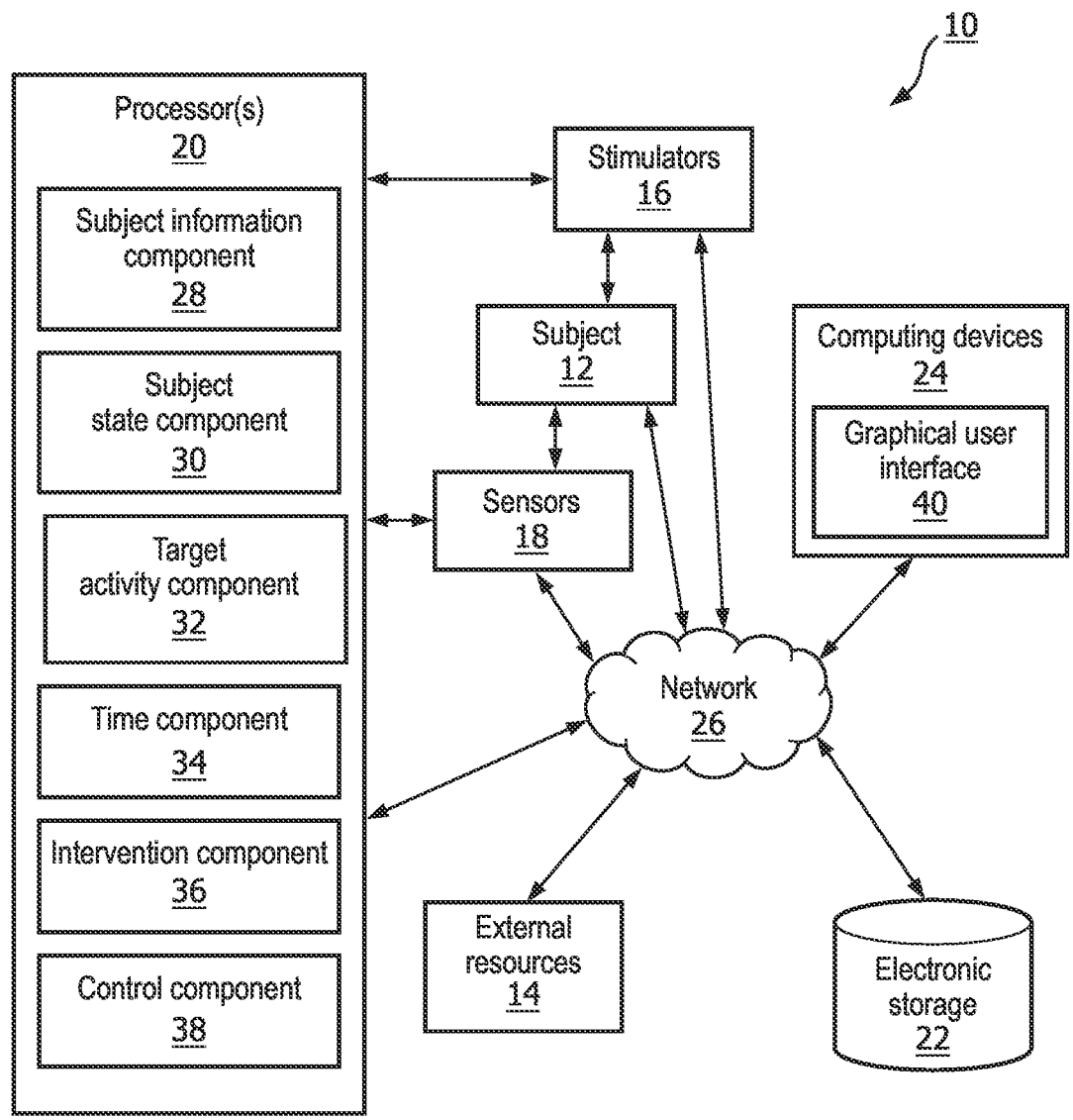
FIG. 1 is a schematic illustration of a system configured for delivering stimulation to facilitate sleep onset, in accordance with one or more embodiments.

As used herein, the singular form of "a," "an," and "the" include plural references unless the context clearly dictates otherwise. As used herein, the term "or" means "and/or" unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Sensory stimulation solutions to help users fall asleep are known. For example, WO2005055802A2 and WO2014118654A1, the content of which is incorporated by reference in its entirety, describe systems and methods for delivering sensory stimulation to help sleep onset. However, there is a need for solutions that provide users with recommendation related to timing and duration of sensory stimulation in order to facilitate falling asleep. The present disclosure overcomes deficiencies in the prior art systems.

Sensory stimulation is known to affect the autonomic nervous system (ANS) activity. For example, vibratory stimulation may be used to alleviate stress by stimulating a response from the parasympathetic nervous system (PNS). Non-invasive whole body vibration (WBV) may be used to regulate the ANS activity and thereby induce a relaxation effect. WBV suppresses sympathetic nervous system (SNS) activity and improves bodily functions, which can be useful for stress management. For example, a facial vibrotactile stimulation of 89 Hz increases salivation, heart rate variability (HRV), and constricts pupils. A vibratory stimulation of 140 Hz on the forearm and wrist increases HRV. These effects on the salivation, HRV, and pupils are indicators of higher PNS activity as a result of the vibratory stimulation. For subjects suffering from insomnia, at sleep onset, differences in HRV between Insomnia with normal objective sleep duration I-NSD and Insomnia with short sleep duration I-SSD clusters suggest attenuated parasympathetic activity in I-SSD ($P<0.05$).

Another method for stimulation is the Bilateral Alternating Stimulation in Tactile form (BLAST) technology. BLAST technology may be used to reduce the sympathetic activity, resulting in a stress reducing effect in individuals with anxiety. BLAST technology is believed to facilitate easier access to positive memories, resulting in a relaxed state. In some cases, alternating bilateral tactile vibratory stimulations may result in an alternating pattern of activations of the contralateral hemispheres of the brain increasing the functional connectivity between the two hemispheres which has beneficiary effects on memory retrieval. However, users of current vibratory stimulation to fall asleep do not receive enough recommendations about when and for howlong they have to use vibration to facilitate falling asleep. Some even give conflicting recommendations about duration of use: 5 minutes in the main product brochure but 15 minutes in the detailed use-case. Unclear recommendations or conflicting instructions can actually exacerbate insomnia issues.

Tests have showed that ANS depends on circadian parameters of the subject. For example, PNS was quantified multiple times in a day: 1) morning, 2) pre-sleep period, and 3) during slow-wave sleep (SWS). It was found that PNS decreased significantly from the morning (0.22) to the pre-sleep period (0.19), before it increased to its maximum during SWS (0.33). In contrast, SNS activity was similar in each of the three conditions (0.07, 0.06, and 0.05 for morning, pre-sleep and SWS, respectively). Thus, sleep-anticipatory changes in PNS do not seem to occur, as it would be predicted on the basis of a circadian influence on the PNS. Instead the increased PNS activity appears to be sleep dependent. Changes in the autonomic nervous system activity profile, similar to those seen during nocturnal sleep have been observed during daytime napping in healthy young adults.

Figure 2:
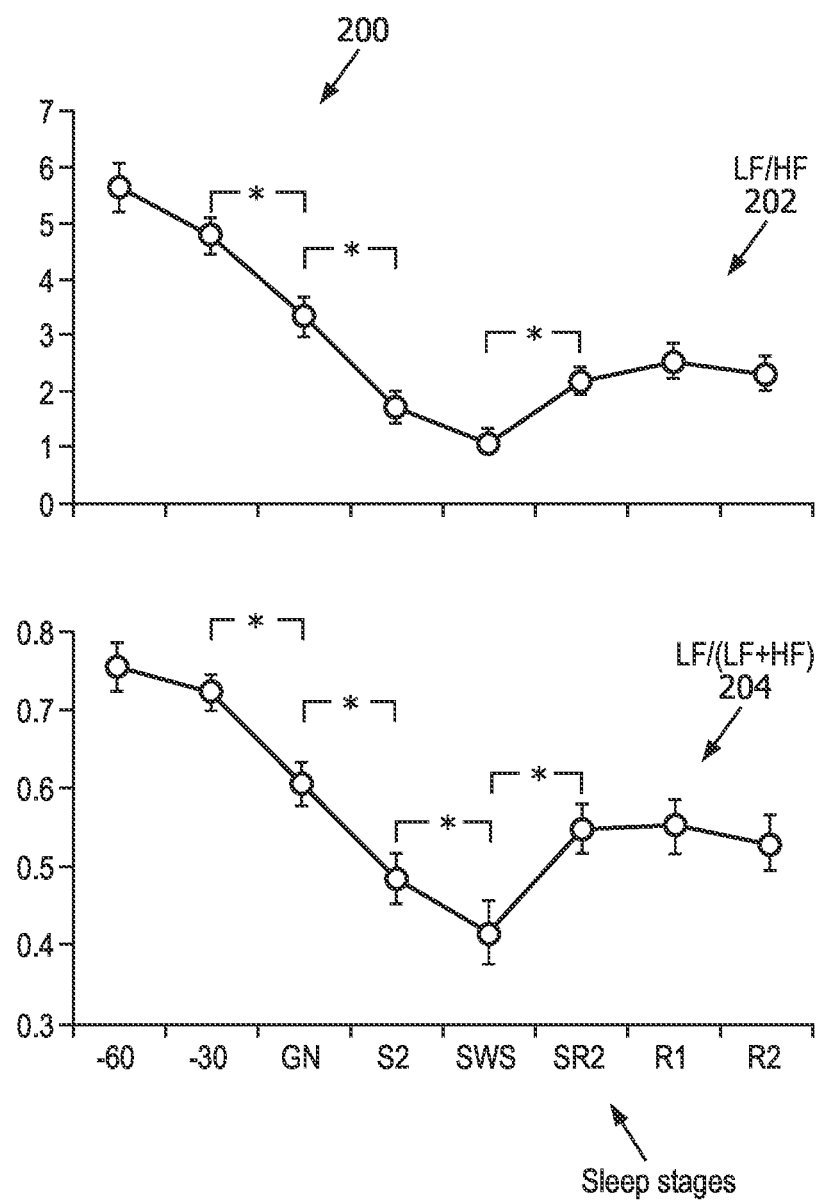
FIG. 2 illustrates an example of heart rate variability HRV before sleep onset and at the onset of different sleep stages.
Figure 3:
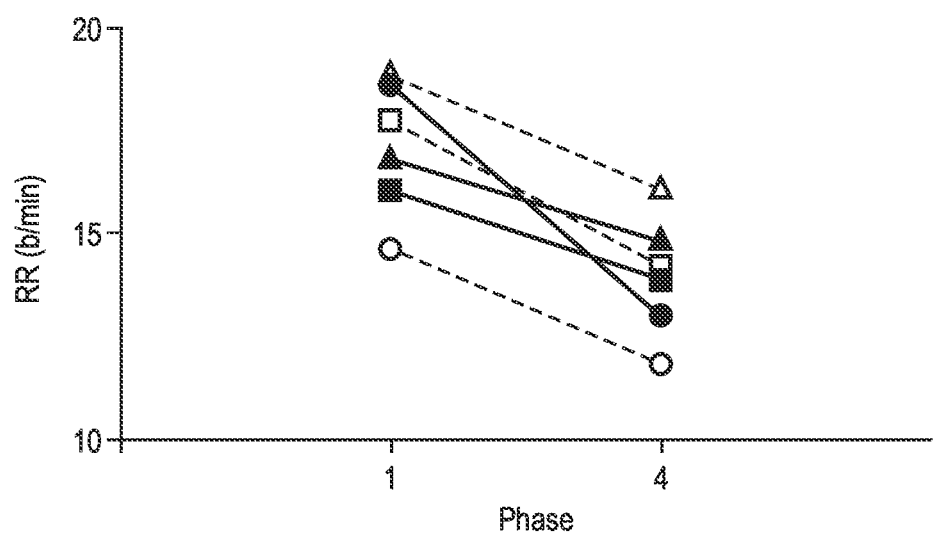
FIG. 3 illustrates example representation of heart rate at different sleep phases.

FIG. 2 illustrates an example 200 of heart rate variability HRV before sleep onset and at the onset of different sleep stages. There is a clear decline in the ratio of the low frequency (LF) to high frequency (HF) component of HRV (LF/HF) 202, and in the normalized LF (LF/(LF+HF)) 204, prior to the sleep onset (e.g., at 60 min prior (−60), and at 30 min (−30)), at sleep onset and during consecutive sleep stages (stage 2 (S2), and slow wave stage (SWS)). Body temperature (not shown in FIG. 2) follows the same decline. and increases following each spontaneous arousal (e.g., SR2). FIG. 3 illustrates an example 300 of heart rate HR during sleep phases Phase 1(wake) and Phase 4 (stable sleep). As can be seen from the figure, HR decreases at each transition into sleep (e.g., from wake to stable sleep).

In some embodiments, system 10, is configured to deliver stimulation to a subject for facilitating sleep onset. In some embodiments, system 10 is configured to characterize an initial state of the user, recommend a stimulation setting, and utilize a model to determine the duration of stimulation to lead the user into a state favoring falling asleep. System 10 is advantageous compared to previous systems in that the engine that determines the duration and type of vibratory stimulation is based on a model quantifying the physiological effects of the stimulation depending on the time of the day (circadian dependent model). Furthermore, system 10 may shorten sleep onset latency. reduce the occurrence of sleep maintenance insomnia. improve overall sleep hygiene. In some embodiments, system 10 is as input the current time, the current PNS activation state, and the time at which sleep onset is desired. The output is the duration and turn-on time of the intervention. In some embodiments, system 10 is configured to receive as an input the desired time for sleep onset and automatically starts and stops the vibratory stimulation without further user input. In some embodiments, system 10 may be configured such that type of stimulation and duration thereof behave differently depending on time of the day.

In some embodiments, system 10 comprises one or more of stimulator(s) 16, sensor(s) 18, a processor 20, electronic storage 22, client computing platform(s) 24, a network 26, and/or other components. In FIG. 1, stimulator(s) 16, sensor(s) 18, processor 20, electronic storage 22, and client computing platform(s) 24 are shown as separate entities. In some embodiments, some and/or all of the components of system 10 and/or other components may be grouped into one or more singular devices (e.g., a wearable device or other user device). In some embodiments, a wearable device may include a housing, one or more sensors (e.g., sensors 18), processors (e.g., processors 20), stimulators (e.g., stimulators 16), or other components. Any combination or subcombination of the sensors 18, processors 20 (and components thereof), storage 22, network 26, computing devices 24 and stimulators 16, may be co-located in a single housing, or alternatively each component may be housed in individual housings. Such sensors, processors, stimulators, and other components of the wearable device may communicate with one another via wired or wireless connections. It should be noted that, although some embodiments are described herein with respect to a wearable device performing certain operations, one or more such operations may be performed by one or more other components (e.g., one or more servers, client devices, etc.). As an example, such other components (e.g., one or more servers, client devices, etc.) may include one or more processor components that are the same as or similar to subsystems components 28-38.

Figure 4:
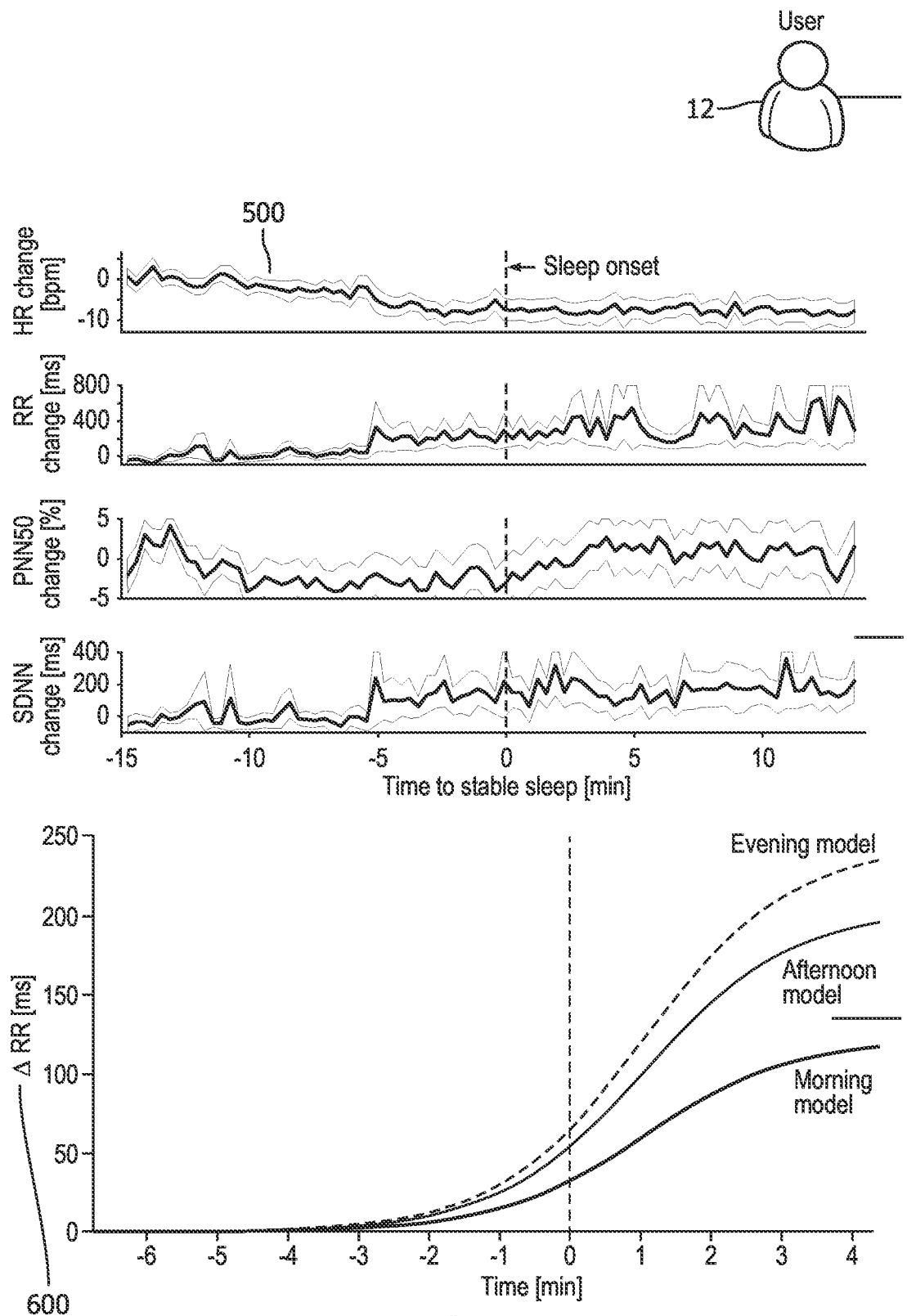
FIG. 4 illustrates an example diagram of a system configured for delivering stimulation to facilitate sleep onset, in accordance with one or more embodiments.
Figure 4:
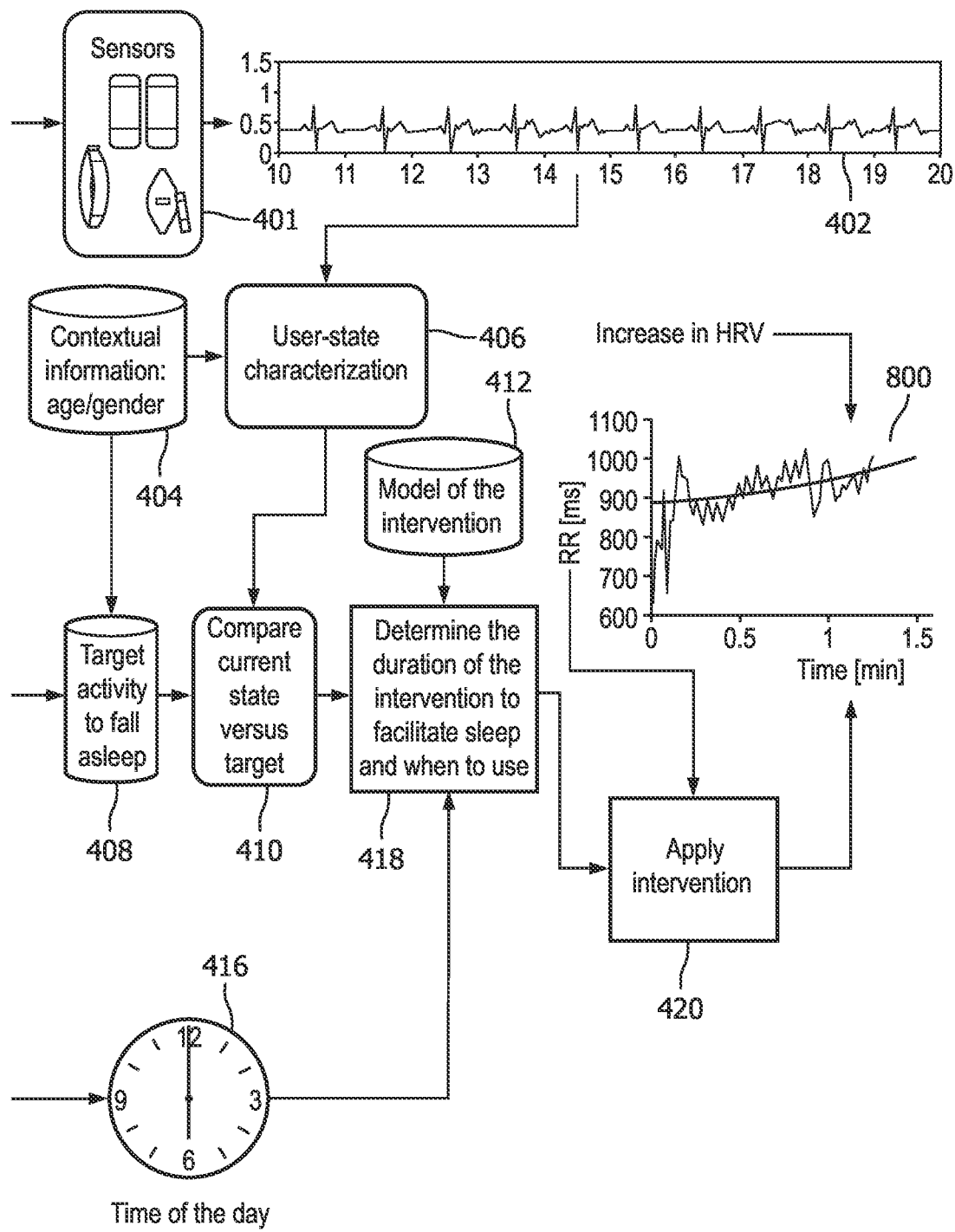

Sensor(s) 18 is configured to generate output signals conveying information related to the current state of the subject. In some embodiments, the current state of the subject may be determined based on one or more physiological parameters of subject 12. In some embodiments, the physiological parameters of the subject may include cardiac activity of subject 12, one or more of heartbeat, heart rate, heart rate variability, microvascular blood volume, galvanic skin resistance, brain activity, and/or other physiological parameters. In some embodiments, the one or more physiological parameters of subject 12 may include one or more of oximetry parameters, pulse, temperature, blood pressure, and/or other vital signs of the subject). In some embodiments, the one or more sensors may include one or more of a heart rate sensor, a temperature sensor, an oximeter, a blood pressure sensor, and/or other vital signs sensors. In some embodiments, the one or more sensor(s) may include one or more of an electrocardiogram (ECG), a photoplethysmograph (PPG), an electroencephalogram (EEG), a galvanic skin resistance (GSR) sensor, and/or other sensors. In some embodiments, sensor(s) 18 may include a movement sensor, an accelerometer, actimetry sensor, a camera, a breathing monitor, and/or other sensors configured for monitoring the subject state. In some embodiments, one or more of sensor(s) 18 may be located on the chest of subject 12, and/or be configured as a bracelet on a wrist band of subject 12, and/or be located on another limb of subject 12). Although sensor(s) 18 is illustrated at a single location near subject 12, this is not intended to be limiting. Sensor(s) 18 may include sensors disposed in a plurality of locations, such as for example, coupled (in a removable manner) with clothing of subject 12, worn by subject 12 (e.g., as a headband, wristband, etc.), positioned to point at subject 12 while subject 12 sleeps (e.g., a camera that conveys output signals related to movement of subject 12), and/or in other locations. In some embodiments, sensor(s) 18 may be included in a wearable device. The wearable device may be any device that is worn, or that is in full or partial contact with any body parts of the subject. FIG. 4 (described below) shows an example of a wearable device that may be in the form of a wristband 401. In some embodiments, the wearable device may be configured to generate output signals conveying information related to heart rate, heart rate variability, microvascular blood volume, galvanic skin resistance, brain activity, and/or other physiological parameters. The output signals may be transmitted to a computing device (within or outside of the wearable device) wirelessly and/or via wires. For example, in some embodiments, system 10 of FIG. 1 may be similar to wearable device 401 of FIG. 4 or may be included in a wearable device similar to wearable device 401 of FIG. 4. In some embodiments, some or all components of system 10 of FIG. 1 may be included in a wearable device similar to wearable device 401 of FIG. 4.

Stimulator(s) 16 is configured to provide stimulation to subject 12. In some embodiments, stimulation provided to the subject may be peripheral stimulation (e.g., sensory, electric, magnetic, etc.). In some embodiments, stimulator(s) In some embodiments, other types of stimulation may be considered. Stimulator(s) 16 may be configured to provide stimulation to subject 12 prior, during, and/or after a sleep session. For example, in some embodiments, stimulation may be provided before a sleep session to facilitate sleep onset. In some embodiments, the stimulation may be provided to subject 12 during a current sleep session to help the subject to stay asleep. For example, stimulator(s) 16 may be configured to provide stimulation to subject 12 during a sleep session to induce sleep slow waves and/or enhance sleep slow waves in subject 12.

In some embodiments, stimulation provided by stimulator(s) 16 may include haptic stimulation, auditory stimulation, light stimulation, electrical stimulation, magnetic stimulation, visual stimulation, and/or olfactory stimulation. For example, stimulator(s) 16 may be configured to non-invasive brain stimulation using odors, sounds, visual stimulation, touches, tastes, and/or other stimulation. Examples of stimulator(s) 16 may include one or more of vibratory stimulator, a coil generating a magnetic field to directly stimulate the brain's cortex, light generators, a fragrance dispenser, a music player, a tone generator, a collection of electrodes on the scalp of subject 12, and/or other stimulators.

In some embodiments, one or more parameters of the stimulator(s) (e.g., type of stimulation, time interval, intensity, volume, frequency, etc.) may be adjusted. For example, based on output signals from sensor(s) 18 related to subject state. In some embodiments, adjustments to one or more parameters of the stimulator(s) may be based on feedback from one or more component of system 10, information from individual subjects, information from individual users (e.g., healthcare professionals, caregivers, etc.), therapies, manufacturer settings, and/or other information. For example, one or more parameters of the stimulations may be adjusted between upper and lower thresholds. The upper and lower thresholds for the stimulation parameters may be determined for each subject based on previous sleeping sessions, previous interventions, or may be based on similarities between the subject and one or more subjects having one or more similarities with the subject (e.g., brain activity, demographic information, vital sign information, medical/health condition information, treatment history information, similar desired outcome, and/or other similarities.)

In some embodiments, one or more of stimulator(s)16 is illustrated at a single location near subject 12, this is not intended to be limiting. one or more of stimulator(s)16 may be disposed in a plurality of positions on the subject, such as for example, wrist (e.g., in a wristband), forearm, head, legs, chest, etc.

Processor 20 is configured to provide information processing capabilities in system 10. As such, processor 20 may include one or more of a digital processor, an analog processor, and a digital circuit designed to process information, an analog circuit designed to process information, a state machine, and/or other mechanisms for electronically processing information. Although processor 20 is shown in FIG. 1 as a single entity, this is for illustrative purposes only. In some embodiments, processor 20 may include a plurality of processing units. These processing units may be physically located within the same device (e.g., a server), or processor 20 may represent processing functionality of a plurality of devices operating in coordination (e.g., one or more servers, one or more computing devices 24 associated with users, a medical device, stimulator(s) 16, sensor(s) 18, a piece of a hospital equipment, devices that are part of external resources 14, electronic storage 22, and/or other devices.)

As shown in FIG. 1, processor 20 is configured to execute one or more computer program components. The one or more computer program components may comprise one or more of a subject information component 28, a subject state component 30, a target activity component 32, a time component 34, an intervention component 36, a control component 38, and/or other components. Processor 20 may be configured to execute components 28, 30, 32, 34, 36, 38 and/or other components by software; hardware; firmware; some combination of software, hardware, and/or firmware; and/or other mechanisms for configuring processing capabilities on processor 20.

It should be appreciated that although components 28, 30, 32, 34, 36, and 38 are illustrated in FIG. 1 as being co-located within a single processing unit, in embodiments in which processor 20 comprises multiple processing units, one or more of components 28, 30, 32, 34, 36, 38, and/or other components may be located remotely from the other components. The description of the functionality provided by the different components 28, 30, 32, 34, 36, 38 and/or other components described below is for illustrative purposes, and is not intended to be limiting, as any of components 28, 30, 32, 34, 36, and/or 38 may provide more or less functionality than is described. For example, one or more of components 28, 30, 32, 34, 36, and/or 38 may be eliminated, and some or all of its functionality may be provided by other components 28, 30, 32, 34, 36, and/or 38. As another example, processor 20 may be configured to execute one or more additional components that may perform some or all of the functionality attributed below to one of components 28, 30, 32, 34, 36, and/or 38.

Subject information component 28, in some embodiments, may be configured to determine (and/or obtain) information related to subject 12. In some embodiments, information related to subject 12 may include biographical information. For example, biographical information may include demographic information (e.g., gender, ethnicity, age, etc.), vital sign information (e.g., weight, BMI, etc.), medical/health condition information (e.g., a disease type, severity of the disease, stage of the disease, categorization of the disease, symptoms, behaviors, readmission, relapse, etc.), treatment history information (e.g., type of treatments, length of treatment, current and past medications, etc.), and/or other information. In some embodiments, subject information component 28 may include information related to sleep and/or brain activity information (e.g., feedback from previous stimulations, previous brain activity information, previous sleep states information, and/or other sleep and brain activity related information.)

In some embodiments, subject information component 28 may be configured to determine (and/or obtain) information related other subjects. For example, subjects with similar brain activity information, demographic information, vital sign information, medical/health condition information, treatment history information, similar desired outcome (e.g., from sensory simulation), similar sleep information, and/or other similarities with subject 12. It should be noted that the subject information described above is not intended to be limiting. A large number of information related to subjects may exist and may be used with system 10 in accordance with some embodiments. For example, users may choose to customize system 10 and include any type of subject data they deem relevant.

In some embodiments, subject information component 28 may be configured to obtain/extract information from one or more databases (e.g., contextual information database shown in FIG. 4). In some embodiments, different databases may contain different information about subject 12 and/or about other subjects (e.g. similar to subject 12). In some embodiments, some databases may be associated with specific subject information (e.g., a medical condition, a demographic characteristic, a treatment, a therapy, a medical device used, a vital sign information, etc.) In some embodiments, subject information component 28 may be configured to obtain/extract the subject information from external resources 14 (e.g., one or more external databases included in external resources 14), electronic storage 22 included in system 10, one or more medical devices, and/or other sources of information.

Subject state component 30 may be configured to determine (and/or obtain) a state of subject 12. In some embodiments, state of the subject is determined based on output signals from sensor(s) 18. In some embodiments, the state of the subject includes a degree of parasympathetic activity. The degree of parasympathetic activity is useful in quantifying propensity to fall asleep. In some embodiments, a degree of parasympathetic activity may be determined based on cardiac activity of the subject (e.g., ECG, and/or PPG). In the example shown in FIG. 4, an ECG signal is used to determine the state of the user. In this example, the state of the user is characterized using metrics of ANS activity such as heart-rate variability (HRV) (using e.g. RR-duration, heart-rate, or the standard deviation of the RR-duration). In some embodiments, subject information (for example obtained from contextual information database) such as age-range and gender may be used to increase HRV accuracy characterization.

In some embodiments, the subject state is characterized using heart rate variability. HRV is the amount of variability in the time intervals between adjacent heartbeats, i.e. RR. Typically, NN intervals, i.e. RR intervals from which artifacts have been removed are used for further analysis. Time-domain indices of HRV directly quantify NN. Frequency-domain measurements estimate the distribution of absolute or relative power of the NN intervals into four frequency bands: ultra-low frequency (ULF), very-low frequency (VLF), low frequency (LF) and high frequency (HF). This can be achieved by computing the Fast Fourier Transform (FFT) to separate HRV into its component ULF, VLF, LF and HF rhythms that operate within different frequency ranges. The ratio of low frequency to high frequency power (LF/HF ratio) may estimate the relationship between the sympathetic nervous system (SNS) and parasympathetic nervous system (PNS) activity. In some embodiments, the LF power is generated by the SNS while the HF power is generated by the PNS. Hence a high HF/LF ratio indicates parasympathetic over sympathetic dominance. The standard deviation of the NN intervals (SDNN) is measured in milliseconds. Both SNS and PNS activity contribute to SDNN and it correlates with ULF, VLF, LF band power and total power. pNN50 is the percentage of successive RR intervals that differ by more than 50 milliseconds.

Target component 32 is configured to determine (and/or obtain) a target user state to fall asleep. In operation, in some embodiments, a target state to fall asleep is compared to current state of the user. The difference between the current and target state enables the system to determine one or more characteristics of the stimulation (e.g., type, duration, intensity of the stimulation, etc.). In some embodiments, target component module 32 may be configured to determine a target user state to fall asleep. In some embodiments, the target state may be obtained from a data base within or outside system 10. For example, in some embodiments, the target state may be obtained based on previously determined target state corresponding to the subject. In some embodiments, the target state may be determined based on one or more target state corresponding to other subjects (e.g., subjects similar to subject 12). In some embodiments, the target state may be pre-determined (e.g., by a provider, user, manufacturer, etc.)

Figure 5:
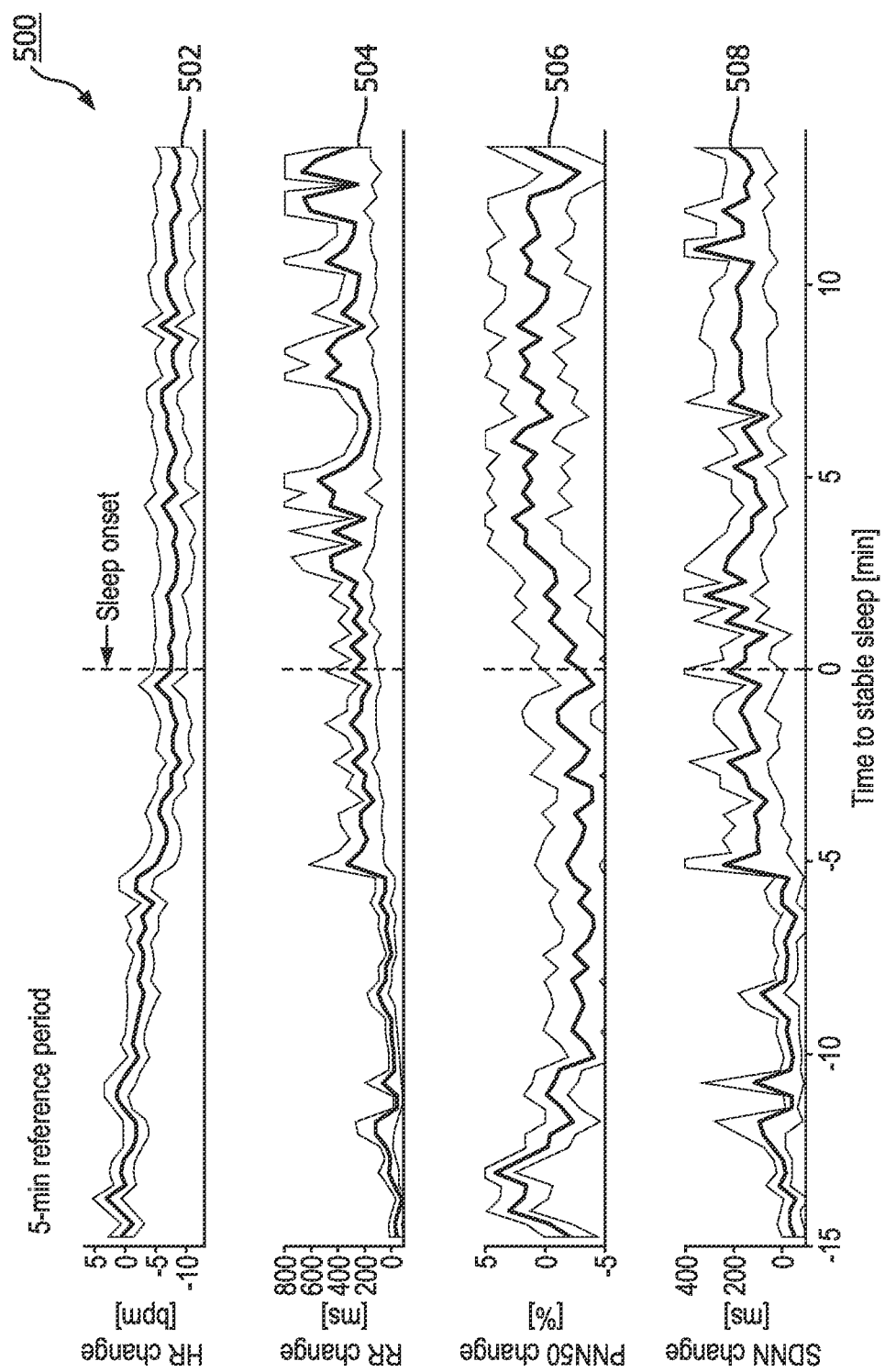
FIG. 5 illustrates a representations of changes in autonomic nervous system activity during the wake to sleep transition, in accordance with one or more embodiments.

In some embodiments, the target state may be determined based on information conveyed by the output signals of sensor(s) 18. For example, target component 32 may be configured to determine the target state based on changes in autonomic nervous system activity preceding sleep onset. FIG. 5 illustrates an example representations of changes in autonomic nervous system activity during the wake to sleep transition, in accordance with one or more embodiments. In FIG. 5, time "0" indicates sleep onset. The polysomnographic (including EEG, ECG, EOG, and EMG) sleep data from an in-lab study with manual sleep staging was used to estimate the changes in heart-rate variability: HR 502, RR 504, PNN50 506, and SDNN 508. Seventy-two nights from 19 subjects were used to estimate the average HRV changes during the transition from wakefulness to sleep. 15 minutes before sleep onset and 15 minutes after sleep onset were analyzed. The five-minute interval between 15 to 10 minutes prior to sleep onset was used as reference with respect to which the HRV change parameters were calculated. The change dynamics in FIG. 5 show that the wake to sleep transition is characterized by a 250-millisecond increase in RR duration, 5% increase in PNN50, and a 200-millisecond increase in SDNN. Given that an increase in RR of −200 milliseconds favor sleep initiation, the model $$\Delta RR(t) = a_j + \frac{b_j}{1 + e^{-c_j t}}$$

(where j refers to the time of the day: morning, afternoon, or evening) permits to estimate the time needed by solving the equation:

$$t = \frac{1}{c_j} \log\left(\frac{200 - a_j}{a_j + b_j - 200}\right).$$

Figure 6:
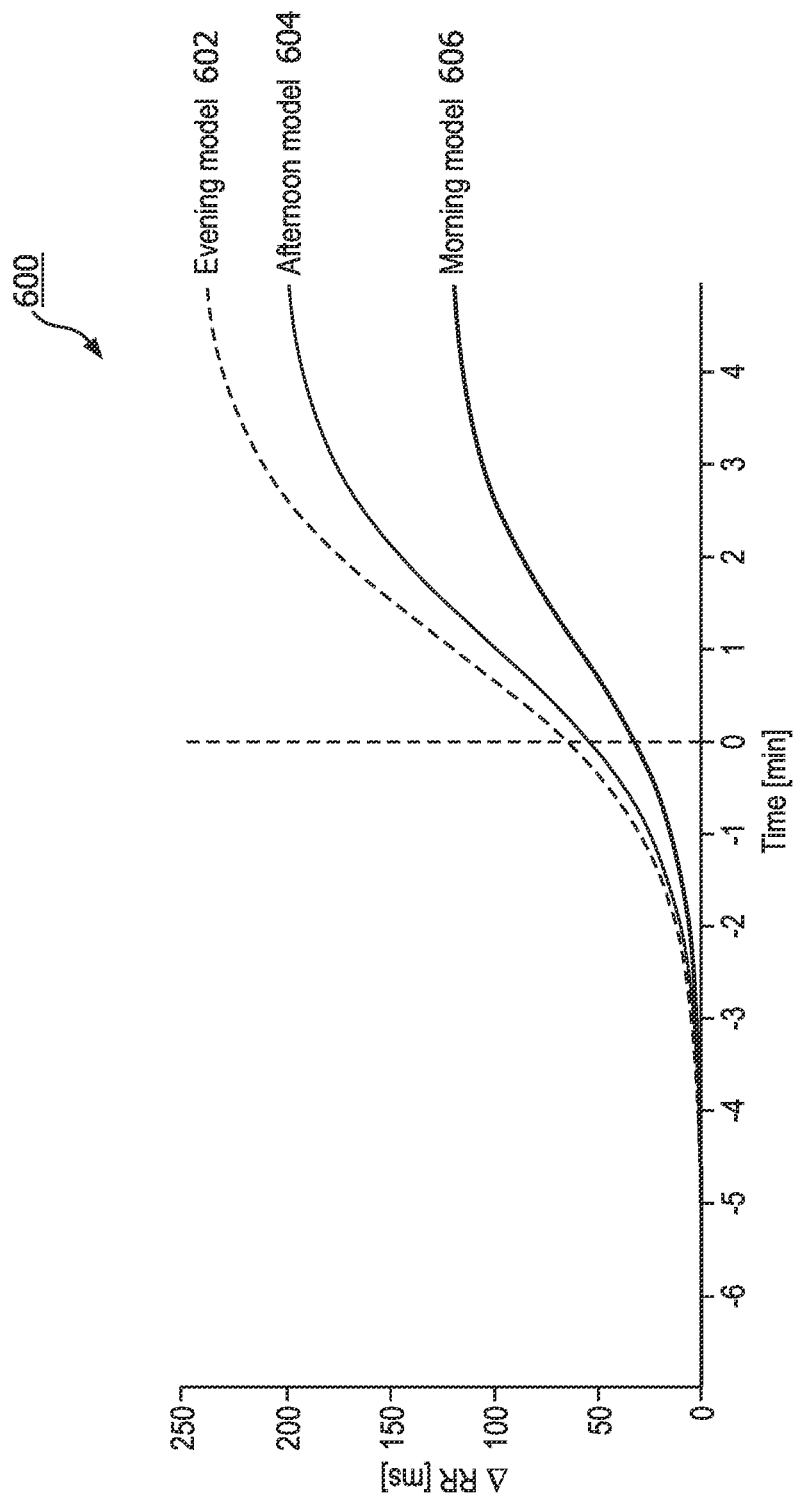
FIG. 6 illustrates an example circadian-dependent model of the effect of the vibratory stimulation on heart-rate, in accordance with one or more embodiments.

Returning to FIG. 1, in some embodiments, time component 34 may be configured to determine a current time of day. In some embodiments, time of the day is used to determine duration and type of stimulation. Physiological effects of the stimulation depend on the time of the day. FIG. 6 illustrates an example circadian-dependent model 600 of the effect of the vibratory stimulation on heart-rate, in accordance with one or more embodiments. The circadian-dependent model 600 is a dynamic model of effectiveness of the vibratory intervention on the duration of RR (inter-beat) intervals. The increase in RR duration (i.e. heart-rate decrease) per unit of time depends on circadian factors as the intervention is more effective in the evening 602 compared to morning 606 or afternoon 604. In other words, the type of stimulation and duration thereof behave differently depending on time of the day. In some embodiments, system 10 (e.g., intervention component 36 described below) may be configured to take as input the current time, the current PNS activation state, and the time at which sleep onset is desired. The output (e.g., recommendation) of the system is the duration and turn-on time of the intervention. In some embodiments, system 10 is configured to automatically start and stop the vibratory stimulation without further user input based on the determined duration and turn-on time of the intervention.

Returning to FIG. 1, intervention component 36 is configured to determine one or more parameters of stimulation to be delivered to the subject at a given time (or before, or around the given time). In some embodiments, the one or more stimulation parameters may include (type, duration, timing, time interval, intensity, volume, frequency, etc.) In some embodiments, intervention component 36 is configured to determine one or more parameters of the stimulation based on a difference between the targeted state and the current state of the subject. For example, intervention component 36 may receive information related to the subject current state from subject state component 30. Intervention component 36 may be configured to determine a difference between the current state and the target state. Based on the determined difference, intervention component 36 determines one or more parameters of the stimulation to be delivered to the subject (e.g., type, duration, timing, time interval, intensity, volume, frequency, etc.) In some embodiments, the difference between the current state and the target state may be determined by one or more components other than intervention component 36 (e.g., target component, subject state component, and/or other component within or outside system 10). In some embodiments, intervention component 36 is configured to determine one or more parameters of the stimulation based on the time of day and/or the desired time for sleep onset. For example, as explained above (and shown in FIG. 6), increase in RR duration (i.e. heart-rate decrease) per unit of time depends on circadian factors as the intervention is more effective in the evening compared to morning or afternoon.

Figure 7:
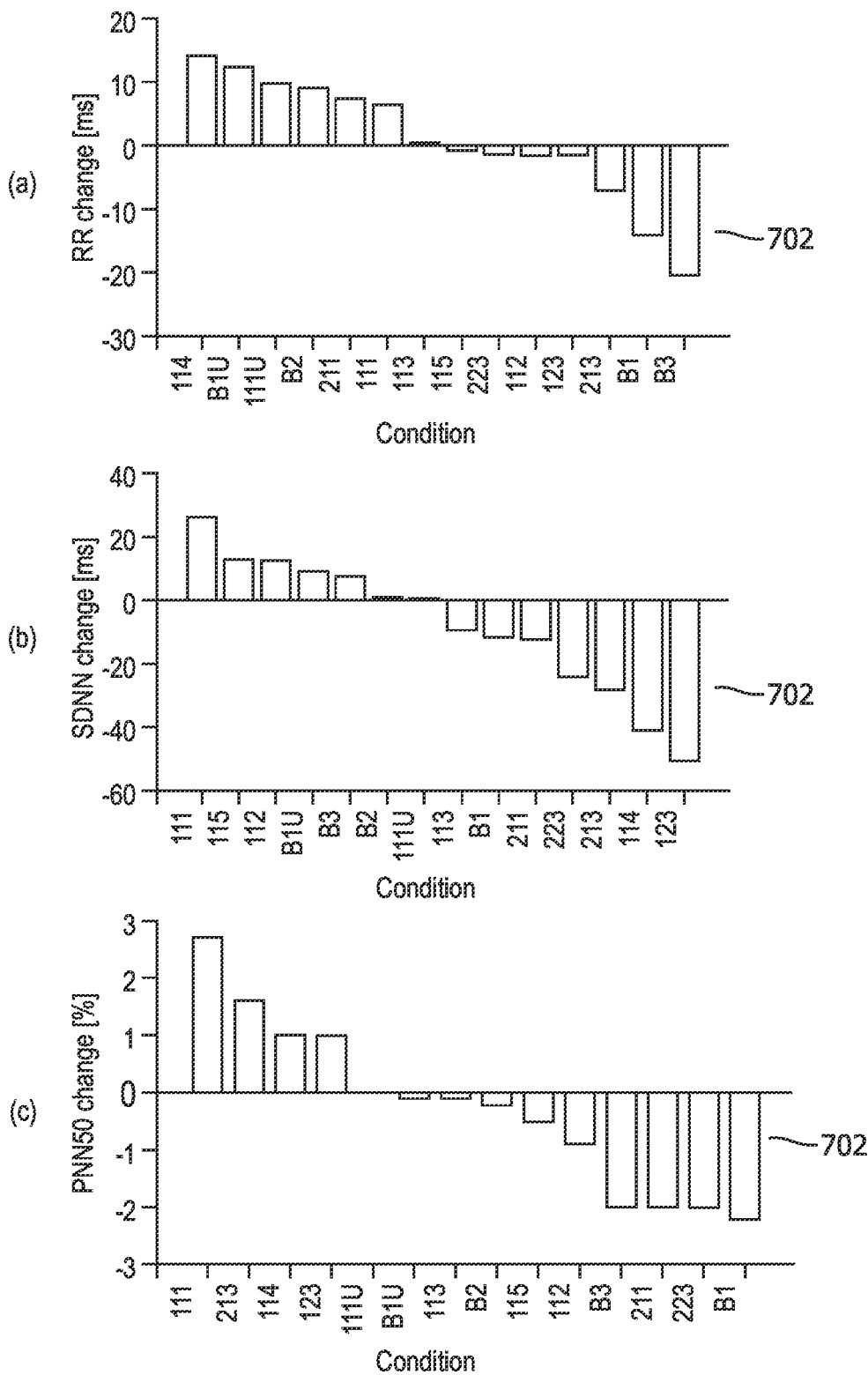
FIG. 7 illustrates examples of autonomic nervous system activity changes based on type of stimulation, in accordance with one or more embodiments.

Control component 38 is configured to control stimulator(s) 16 to provide stimulation to subject 12. In some embodiments, control component 38 may be configured to cause stimulator(s) 16 to provide stimulation, based on the one or more stimulation parameters determined by intervention component 36. Control component 38 may be configured to control stimulator(s) 16 to provide stimulation to subject 12 prior to a sleep session, during a current sleep session, after a sleep session, and/or at other times. In some embodiments, control component 38 may be configured to control stimulator(s) 16 to adjust the stimulation in real-time (or near real time) based on one or more signals from sensor(s) 18 (e.g., related to physiological parameters.) In some embodiments, control component 38 may be configured to automatically deliver a type of vibratory stimulation. This can be accomplished by considering a database of type of stimulation versus autonomic effect as shown in FIG. 7 described below. In some embodiments, control component may be configured to adjust stimulation between an upper threshold and a lower threshold. The upper thresholds and a lower thresholds may be determined based on information related to subject 12, information related to subjects similar to subject 12, and/or based on other parameters determined by a user (e.g., healthcare professional, caregiver, etc.), and/or one or more components within or outside of system 10.

Figure 8:
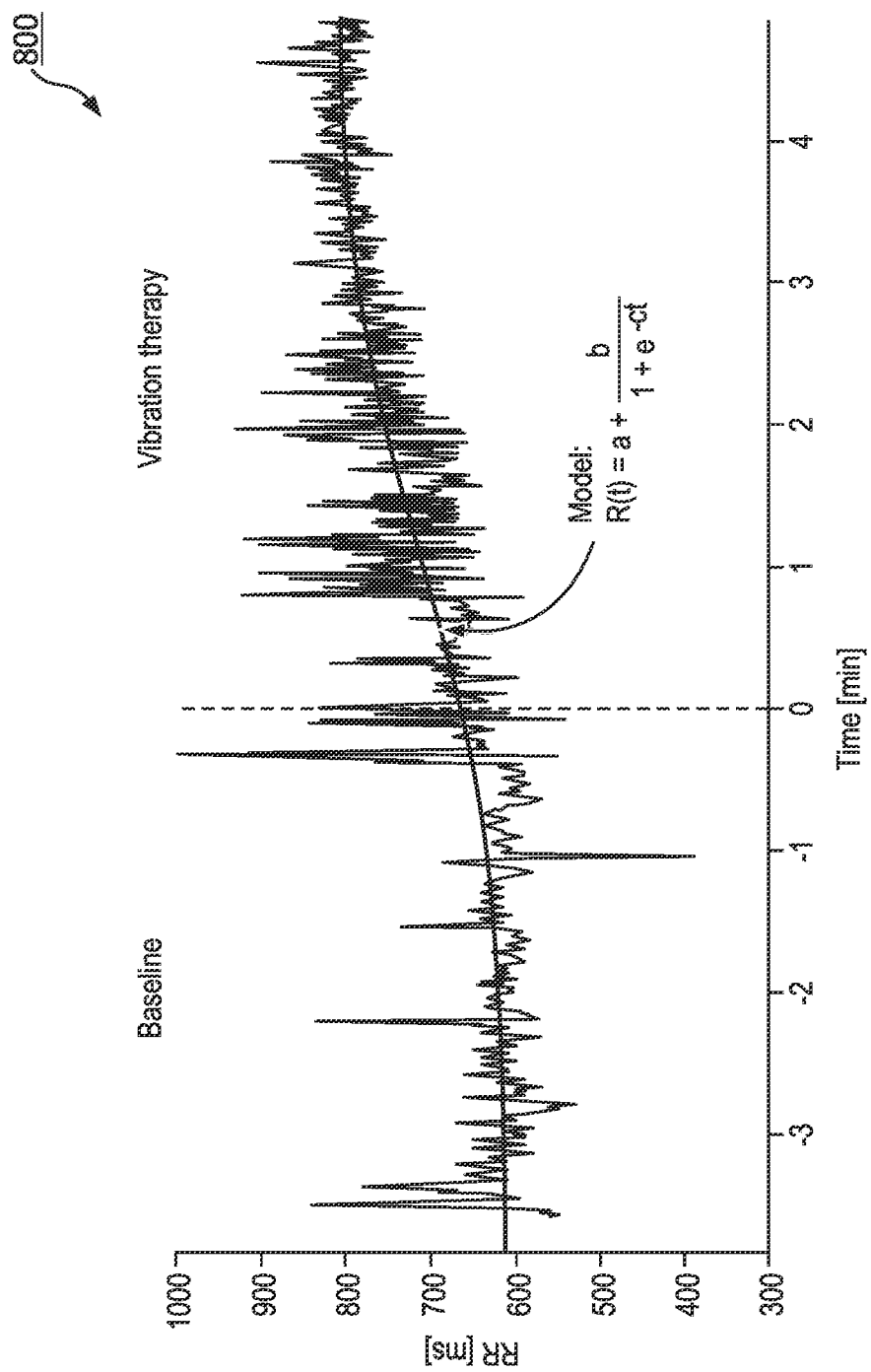
FIG. 8 illustrates an example of data showing the effect of vibration on increasing the duration of the RR interval, in accordance with one or more embodiments.

FIG. 7 illustrates examples of autonomic activity changes based on type of stimulation, in accordance with one or more embodiments. The examples include condition (a) representing average RR change, condition (b) representing average SDNN change, and condition (c) representing average PNN50 change. To model the effect of vibratory stimulation on autonomic activity, an experiment was conducted where vibratory stimulation was applied while the ECG signal was measured. Eight volunteers participated in the experiment which consisted in testing 14 types of vibratory stimulation. For each type of vibration 702, an approximate 5-minute long baseline period was applied followed by the active condition where the vibration was applied. Throughout both, baseline and active conditions, the ECG was recorded. The effect of the vibration on heart-rate variability was evaluated by comparing the average RR duration, the SDNN, and PNN50 between the active and respective baseline. The higher the change active to baseline is, the higher HRV is. The average changes, across the subjects are shown in FIG. 8. Selecting the top four vibration types 702 (i.e. 114, 111, 115, and 112), a model of effectiveness was estimated by analyzing the instantaneous RR change between the active and vibration conditions. FIG. 8 illustrates an example of data showing the effect of vibration on increasing the duration of the RR interval. FIG. 8 shows the RR increase (i.e. heart-rate decrease) due to the stimulation. The temporal dynamics can be best modeled by a sigmoidal fit. FIG. 8 illustrates an example of data showing the effect of vibration on increasing the duration of the RR interval. The stimulation starts at time "0". A sigmoid function was fit to model R(t) versus time:

$$R(t) = a + \frac{b}{1 + e^{-ct}}$$

FIG. 4 is a schematic illustration of a system configured for delivering stimulation to facilitate sleep onset, in accordance with one or more embodiments. The system in FIG. 4 includes a wearable device 401. Wearable device 401, include one or more sensors(s) (e.g., sensors 18 of FIG. 1) configured to output one or more signals 402 indicating one or more physiology parameters of subject 12. An initial state 406 of the subject corresponding to at least one physiological parameter(e.g., HR) is determined. In some embodiments, the system is configured to obtain contextual information 404 related to the subject (e.g., biographical information). A target intervention to fall asleep 408 is determined based on the contextual information 404 and/or based on information from a target activity database. The target activity database may include information from previous data analysis 500 (described in FIG. 5). In some embodiments, one or more parameters of stimulation intervention 418 is determined. In some embodiments, the one or more parameters of stimulation intervention may be determined based on the subject initial state 406 (e.g., based on comparison 410 between the initial state and the target state). In some embodiments, the one or more parameters of stimulation intervention may be determined based on time of the day 416. The time of day is determined based on model 600 (described in FIG. 6). In some embodiments, one or more parameters of the intervention may be obtained from an intervention database 412. In some embodiments, one or more parameters of stimulation intervention 418 includes duration and timing of the stimulation. In some embodiments, the stimulation is provided 420. A feedback may be received after the stimulation is applied. The feedback may be based on model 800 (described in FIG. 8). In some embodiments, the stimulation may be adjusted based on the feedback.

Returning to FIG. 1, system 10 may include one or more of external resources 14, electronic storage 22, client computing platform(s) 24, network 26, and/or other components, all being communicatively coupled via a network 26.

External resources 14 include sources of patient and/or other information. In some embodiments, external resources 14 include sources of patient and/or other information, such as databases, websites, etc., external entities participating with system 10 (e.g., a medical records system of a healthcare provider that stores medical history information for populations of patients), one or more servers outside of system 10, a network (e.g., the internet), electronic storage, equipment related to Wi-Fi technology, equipment related to Bluetooth® technology, data entry devices, sensors, scanners, and/or other resources. In some embodiments, some or all of the functionality attributed herein to external resources 14 may be provided by resources included in system 10. External resources 14 may be configured to communicate with processor 20, computing devices 24, electronic storage 22, and/or other components of system 10 via wired and/or wireless connections, via a network (e.g., a local area network and/or the internet), via cellular technology, via Wi-Fi technology, and/or via other resources.

Electronic storage 22 includes electronic storage media that electronically stores information. The electronic storage media of electronic storage 22 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 22 may be (in whole or in part) a separate component within system 10, or electronic storage 22 may be provided (in whole or in part) integrally with one or more other components of system 10 (e.g., computing devices 18, processor 20, etc.). In some embodiments, electronic storage 22 may be located in a server together with processor 20, in a server that is part of external resources 14, in a computing device 24, and/or in other locations. Electronic storage 22 may include one or more of optically readable storage media (e.g., optical disks, etc.), magnetically readable storage media (e.g., magnetic tape, magnetic hard drive, floppy drive, etc.), electrical charge-based storage media (e.g., EPROM, RAM, etc.), solid-state storage media (e.g., flash drive, etc.), and/or other electronically readable storage media. Electronic storage 22 may store software algorithms, information determined by processor 20, information received via a computing device 24 and/or graphical user interface 40 and/or other external computing systems, information received from external resources 14, stimulators 16, sensors 18, and/or other information that enables system 10 to function as described herein.

Client computing platform(s) 24 is configured to provide an interface between system 10 and subject 12, and/or other users through which subject 12 and/or other users may provide information to and receive information from system 10. For example, client computing platform(s) 24 may display a representation of the output signal from sensors 18 (e.g., an EEG, 2D/3D images, video, audio, text, etc.) to a user. This enables data, cues, results, instructions, and/or any other communicable items, collectively referred to as "information," to be communicated between a user (e.g., subject 12, a doctor, a caregiver, and/or other users) and one or more of stimulator(s) 16, processor 20, electronic storage 22, and/or other components of system 10.

Examples of interface devices suitable for inclusion in client computing platform(s) 24 comprise a keypad, buttons, switches, a keyboard, knobs, levers, a display screen, a touch screen, speakers, a microphone, an indicator light, an audible alarm, a printer, a tactile feedback device, and/or other interface devices. In some embodiments, client computing platform(s) 24 comprises a plurality of separate interfaces. In some embodiments, client computing platform(s) 24 comprises at least one interface that is provided integrally with processor 20, stimulator(s) 16, sensor(s) 18, and/or other components of system 10. Computing devices 24 are configured to provide interfaces between caregivers (e.g., doctors, nurses, friends, family members, etc.), patients, and/or other users, and system 10. In some embodiments, individual computing devices 24 are, and/or are included, in desktop computers, laptop computers, tablet computers, smartphones, and/or other computing devices associated with individual caregivers, patients, and/or other users. In some embodiments, individual computing devices 24 are, and/or are included, in equipment used in hospitals, doctor's offices, and/or other medical facilities to patients; test equipment; equipment for treating patients; data entry equipment; and/or other devices. Computing devices 24 are configured to provide information to, and/or receive information from, the caregivers, patients, and/or other users. For example, computing devices 24 are configured to present a graphical user interface 40 to the caregivers to facilitate display representations of the data analysis, and/or other information. In some embodiments, graphical user interface 40 includes a plurality of separate interfaces associated with computing devices 24, processor 20 and/or other components of system 10; multiple views and/or fields configured to convey information to and/or receive information from caregivers, patients, and/or other users; and/or other interfaces.

In some embodiments, computing devices 24 are configured to provide graphical user interface 40, processing capabilities, databases, and/or electronic storage to system 10. As such, computing devices 24 may include processors 20, electronic storage 22, external resources 14, and/or other components of system 10. In some embodiments, computing devices 24 are connected to a network (e.g., the internet). In some embodiments, computing devices 24 do not include processors 20, electronic storage 22, external resources 14, and/or other components of system 10, but instead communicate with these components via the network. The connection to the network may be wireless or wired. For example, processor 20 may be located in a remote server and may wirelessly cause display of graphical user interface 40 to the caregivers on computing devices 24. As described above, in some embodiments, an individual computing device 18 is a laptop, a personal computer, a smartphone, a tablet computer, and/or other computing devices. Examples of interface devices suitable for inclusion in an individual computing device 18 include a touch screen, a keypad, touch-sensitive and/or physical buttons, switches, a keyboard, knobs, levers, a display, speakers, a microphone, an indicator light, an audible alarm, a printer, and/or other interface devices. The present disclosure also contemplates that an individual computing device 18 includes a removable storage interface. In this example, information may be loaded into a computing device 18 from removable storage (e.g., a smart card, a flash drive, a removable disk, etc.) that enables the caregivers, patients, and/or other users to customize the implementation of computing devices 24. Other exemplary input devices and techniques adapted for use with computing devices 24 include, but are not limited to, an RS-232 port, an RF link, an IR link, a modem (telephone, cable, etc.), and/or other devices.

The network 26 may include the Internet and/or other networks, such as local area networks, cellular networks, Intranets, near field communication, frequency (RF) link, Bluetooth™, Wi-Fi™, and/or any type(s) of wired or wireless network(s). Such examples are not intended to be limiting, and the scope of this disclosure includes embodiments in which external resources 14, stimulator(s) 16, sensor(s) 18, processor(s) 20, electronic storage 22, and/or client computing platform(s) 24 are operatively linked via some other communication media.

Figure 9:
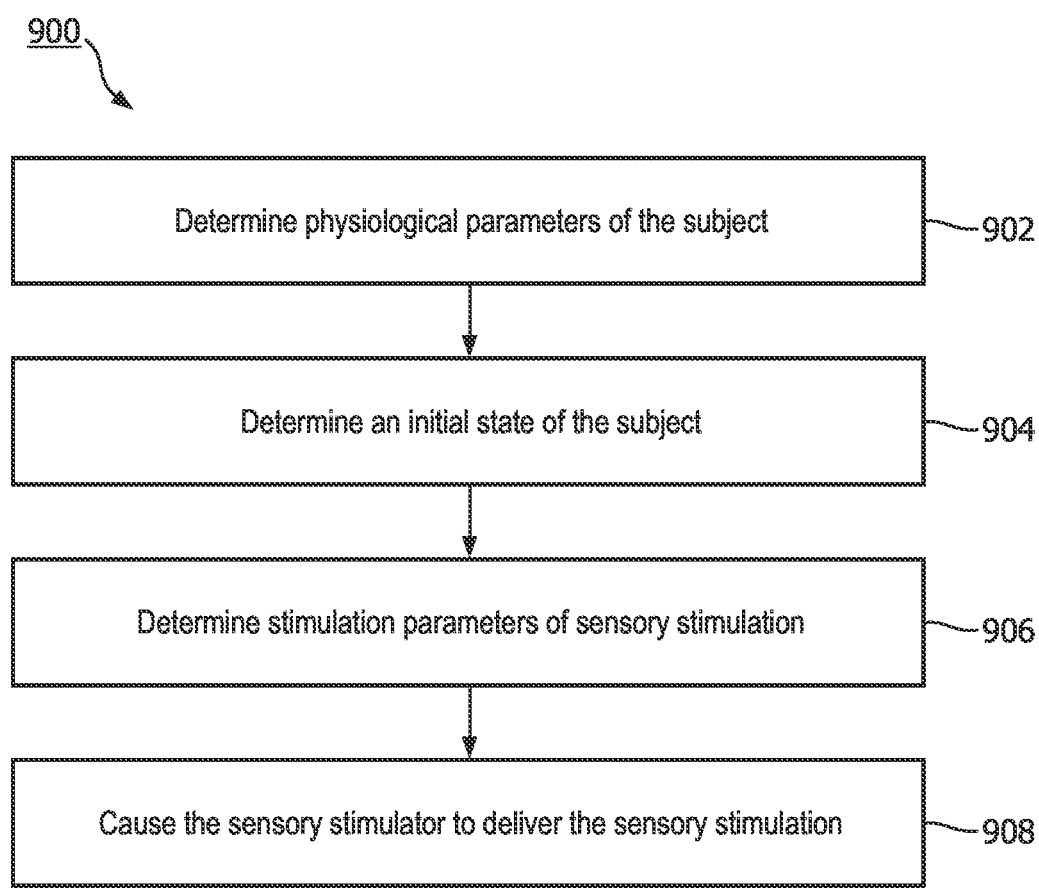
FIG. 9 illustrates a method for delivering stimulation to facilitate sleep onset, in accordance with one or more embodiments.

FIG. 9 illustrates a method 900 for delivering sensory stimulation to a subject for facilitating sleep onset. The system comprises one or more sensors, one or more stimulators, one or more physical computer processors, and/or other components. The one or more processors are configured to execute one or more computer program components. The one or more computer program components may comprise a subject information component 28, a subject state component 30, a target activity component 32, a time component 34, an intervention component 36, a control component 38, and/or other components. The operations of method 900 presented below are intended to be illustrative. In some embodiments, method 900 may be accomplished with one or more additional operations not described, and/or without one or more of the operations discussed. Additionally, the order in which the operations of method 900 are illustrated in FIG. 9 and described below is not intended to be limiting.

In some embodiments, method 900 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 900 in response to instructions stored electronically on an electronic storage medium. The one or more processing devices may include one or more devices configured through hardware, firmware, and/or software to be specifically designed for execution of one or more of the operations of method 900.

At an operation 902, output signals indicating one or more physiological parameters of a subject are generated. In some embodiments, operation 902 is performed by a one or more sensors the same as or similar to sensor(18) (shown in FIG. 1 and described herein).

At operation 904, an initial state of the subject is determined based on the output signals from the sensor. In some embodiments, the initial state corresponds to at least one physiological parameter of the subject. In some embodiments, operation 904 is performed by a physical computer processor the same as or similar to processor(s) 20 (shown in FIG. 1 and described herein).

At an operation 906, one or more stimulation parameters of sensory stimulation to be delivered to the subject by the sensory stimulator are determined. In some embodiments, the one or more stimulation parameters may be based on the initial state of the subject. In some embodiments, operation 906 is performed by a physical computer processor the same as or similar to processor(s) 10 (shown in FIG. 1 and described herein).

At an operation 908, the sensory stimulator tis controlled to deliver the sensory stimulation to the subject based on the determined one or more stimulation parameters. In some embodiments, operation 908 is performed by a physical computer processor the same as or similar to processor(s) 20 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for delivering sensory stimulation to a subject for facilitating sleep onset, comprising:
   one or more sensors configured to generate output signals indicating one or more physiological parameters of a subject;
   a sensory stimulator configured to deliver the sensory stimulation to the subject; and
   one or more physical processors operatively connected with the one or more sensors and the sensory stimulator, the one or more physical processors being programmed with computer program instructions which, when executed cause a computer system to:
   determine an initial parasympathetic nervous system (PNS) activation state of the subject indicative of an initial degree of parasympathetic activity of the subject based on the output signals from the one or more sensors, the initial state corresponding to the one or more physiological parameters of the subject and being based on one or more metrics of autonomous nervous system activity of the subject;
   determine a target PNS activation state of the subject indicative of a target degree of parasympathetic activity of the subject to fall asleep;
   determine a difference between the initial PNS activation state and the target PNS activation state;
   determine one or more stimulation parameters of the sensory stimulation to be delivered to the subject by the sensory stimulator based on: (i) the difference; (ii) a current time of day, and (iii) a time at which sleep onset is desired; and
   cause the sensory stimulator to deliver the sensory stimulation to the subject based on the determined one or more stimulation parameters.

2. The system of claim 1, wherein the one or more stimulation parameters of the sensory stimulation include a time and/or a duration of the sensory stimulation.

3. The system of claim 1, wherein the one or more physiological parameters include a heart rate of the subject.

4. The system of claim 1, wherein the one or more sensors include one or more of an electrocardiogram (ECG), photoplethysmograph (PPG), electroencephalogram (EEG), and/or galvanic skin resistance (GSR) sensor.

5. The system of claim 1, wherein the sensory stimulation includes tactile stimulation.

6. The system of claim 1, wherein the one or more physical processors are further configured to:
   obtain stimulation response information from the subject; and
   adjust the one or more stimulation parameters of the sensory stimulation based on the stimulation response information.

7. A method for delivering sensory stimulation to a subject for facilitating sleep onset, comprising:
   generating, with one or more sensors, output signals indicating one or more physiological parameters of a subject;
   determining, with one or more physical processors, an initial parasympathetic parasympathetic activity of the subject based on the output signals from the one or more sensors, the initial state corresponding to the one or more physiological parameters of the subject and being based on one or more metrics of autonomous nervous system activity of the subject;
   determining a target PNS activation state of the subject indicative of a target degree of parasympathetic activity of the subject to fall asleep;
   determining a difference between the initial PNS activation state and the target PNS activation state;
   determining, with one or more physical processors, one or more stimulation parameters of the sensory stimulation to be delivered to the subject by the-a sensory stimulator based on: (i) the difference; (ii) a current time of day, and (iii) a time at which sleep onset is desired; and
   causing, with one or more physical processors, the sensory stimulator to deliver the sensory stimulation to the subject based on the determined one or more stimulation parameters with the sensory stimulator.

8. The method of claim 7, wherein the one or more stimulation parameters of the sensory stimulation include a time and/or a duration of the sensory stimulation.

9. The method of claim 7, wherein the one or more physiological parameters include heart rate of the subject.

10. The method of claim 7, wherein the one or more sensors include one or more of an electrocardiogram (ECG), photoplethysmograph (PPG), electroencephalogram (EEG), and/or galvanic skin resistance (GSR) sensor.

11. The method of claim 7, wherein the sensory stimulation includes tactile stimulation.

12. The method of claim 7, further comprising:
    obtaining, with the one or more physical processors, stimulation response information from the subject; and
    adjusting, with the one or more physical processors, the one or more stimulation parameters of the sensory stimulation based on the stimulation response information.

13. A system for delivering sensory stimulation to a subject for facilitating sleep onset, comprising:
    means for generating output signals indicating one or more physiological parameters of a subject;
    means for delivering the sensory stimulation to the subject;
    means for determining an initial parasympathetic nervous system (PNS) activation state of the subject indicative of a initial degree of parasympathetic activity of the subject based on the output signals from the one or more sensors, the initial state corresponding to the one or more physiological parameters of the subject and being based on one or more metrics of autonomous nervous system activity of the subject;

means for determining a target PNS activation state of the subject indicative of a target degree of parasympathetic activity of the subject to fall asleep;

means for determining a difference between the initial PNS activation state and the target PNS activation state;

means for determining one or more stimulation parameters of the sensory stimulation to be delivered to the subject by the means for delivering the sensory stimulation based on: (i) the difference; (ii) a current time of day, and (iii) a time at which sleep onset is desired; and means for causing the sensory stimulator to deliver the sensory stimulation to the subject based on the determined one or more stimulation parameters.

14. The system of claim 13, wherein the one or more stimulation parameters of the sensory stimulation include a time and/or a duration of the sensory stimulation.

15. The system of claim 13, wherein the one or more physiological parameters include a heart rate of the subject.

16. The system of claim 13, wherein the means for generating output signals includes one or more of an electrocardiogram (ECG), photoplethysmograph (PPG), electroencephalogram (EEG), and/or galvanic skin resistance (GSR) sensor stimulation.

17. The system of claim 13, wherein the sensory stimulation includes tactile stimulation.

18. The system of claim 13, further comprising:
means for obtaining stimulation response information from the subject; and
means for adjusting the one or more stimulation parameters of the sensory stimulation based on the stimulation response information.

* * * * *